United States Patent [19]

Zámbó et al.

[11] Patent Number: 5,565,214
[45] Date of Patent: Oct. 15, 1996

[54] STABLE THERAPEUTIC OIL FILLED SOFT GELATIN CAPSULES

[75] Inventors: István Zámbó, Budapest; Erzsébet Szabó; Sándor Jancsó, both of Debrecen; György Vágó, Budapest; Béla Dános, Budapest; Pál Kaposi, Budapest; Péter Tétényi, Budapest; György Bacsa, Debrecen; Zsuzsanna Emri, Debrecen; Zoltán Gombos, Debrecen, all of Hungary

[73] Assignee: Biogal Gyogyszergyar, Hungary

[21] Appl. No.: 96,058

[22] Filed: Jul. 22, 1993

Related U.S. Application Data

[63] Continuation of Ser. No. 181,439, Apr. 11, 1988, abandoned.

[30] Foreign Application Priority Data

Apr. 17, 1987 [HU] Hungary ................... 1703/87

[51] Int. Cl.⁶ .................................................. A61K 9/48
[52] U.S. Cl. ................. 424/456; 424/195.1; 424/455; 424/451; 514/557; 514/558; 514/560; 514/962
[58] Field of Search ................ 424/408, 455, 424/456; 514/557, 558, 560, 578, 962, 963

[56] References Cited

U.S. PATENT DOCUMENTS

| | | | |
|---|---|---|---|
| 3,126,321 | 3/1964 | Kurtz | 167/83 |
| 3,995,059 | 11/1976 | Fukumaru | 514/625 |
| 4,020,159 | 4/1977 | Herrmann | 424/180 |
| 4,058,594 | 11/1977 | Williams | 424/490 |
| 4,292,304 | 9/1981 | Barels et al. | 424/37 |
| 4,609,403 | 9/1986 | Wittwer et al. | 106/122 |
| 4,727,109 | 2/1988 | Schmidt et al. | 424/455 |
| 4,849,218 | 7/1989 | Hess et al. | 424/94.1 |
| 5,209,978 | 5/1993 | Kosaka et al. | 428/402.2 |

FOREIGN PATENT DOCUMENTS 0106202  4/1984  European Pat. Off. ............... 424/456

OTHER PUBLICATIONS

Burton et al. Human Nutrition p. 197 1988 4th Edition.
Grant & Hacktis Chemical Dictionary, 5th Edititon McGraw Hill, Grant et al., p.10 acid value.
Textbook of Biochemistry West et al. 4th Edition, MacMillan, pp. 142–145, 765, 766.
Kirk–Othmer "Encyclopedia of Chemical Technology" Third Edition, vol. 9 (1980).

*Primary Examiner*—Neil S. Levy
*Attorney, Agent, or Firm*—Schweitzer Cornman & Gross

[57] ABSTRACT

The invention relates to a process for the preparation of therapeutically useful, highly stable soft gelatine capsules containing native oils obtained in the case of vegetable oils by the cold pressing of mainly plant parts, such as seeds, which comprises adjusting the free fatty acid content of the oil to an acid number of from about 0.3 to about 4.5 by mixing oils of identical or different natural source with a different acid number not in excess of about 4.5 and then filling the oil into soft gelatine capsules aromatized from about 0% to about 10% by mass of a perfume.

16 Claims, No Drawings

STABLE THERAPEUTIC OIL FILLED SOFT GELATIN CAPSULES

This is a continuing application of U.S. Ser. No. 181,439, filed on Apr. 14, 1988, which is now abandoned.

FIELD OF THE INVENTION

This invention relates to stable soft gelatine capsules containing native oils and to a process for the preparation of therapeutically useful, highly stable, soft gelatine capsules, containing native oils, mainly vegetable oils, as active ingredient.

As used in the specification and the claims, the term "native oil" means an oil oil bearing parts of vegetable matter and of oil yielding parts of animals.

BACKGROUND OF THE INVENTION

It is to utilize the valuable biological and physiological properties of native oils. In addition to the obvious utilization known for the longest time, i.e. the use of native oils for alimentary purposes, a number of such oils (e.g. almond oil, peanut oil and soybean oil) proved to be very useful as a basic material or therapeutic adjuvant used as a carrier of oily percutaneous or intramuscular injection solutions and as ointment bases in the pharmaceutical and cosmetical industries. The use of various vegetable oils such as wheat-germ oil, maize-germ oil, pumpkin seed oil and cotton seed oil, are also used in alimentation or the prevention of the arteriosclerosis, however, no widespread utilization of vegetable oils has been made for therapeutical purposes.

This can only partly be explained by the fact that no botanically well-defined plant species were available to the users which could provide a defined and reproducible composition of the oils obtained by known methods.

A more significant difficulty in employing these oils in therapeutics was due to the fact that 90 to 95% of the components, mainly lipids, representing the active ingredients of vegetable oils consist of unsaturated or polyunsaturated fatty acid glycerides with a tendency to oxidation (rancidity), raising severe problems of stability, and these problems were not solved heretofore.

Drugs were made available lately in capsule form. This can be explained by many advantageous properties of capsules, such as the rapid biological availability, sustained action, and stability.

The efficiency of the protection of an active ingredient filled into capsules against outside environmental influences (oxygen of the air, moisture, heat) depends on the material of the capsule wall. In addition to gelatine, the wall of the soft gelatine capsules (which are also popular for the relatively simple preparation) also contains liquid, nontoxic additives such as polyethylene glycol, sorbitol and glycerol according to the requirements of modern encapsulating machines (e.g. U.S. Pat. No. 3,239,420).

With increased use of soft gelatine capsules efforts have been made to obtain more chemically resistant capsule walls in order to obtain a stability satisfying the demands raised by extreme conditions, such as in tropical climates, or in the case of particularly sensitive active ingredients.

This problem was attempted to be solved by using a negatively charged organic hydrophilic polymer (see U.S. Pat. No. 2,800,457) or a negatively charged inorganic hydrophilic polymer (see U.S. Pat. No. 3,697,437) instead of phase-separating agents such as inorganic salts that were used earlier in encapsulating processes.

The additives mentioned above form a complex with the positively charged hydrophilic polymer (gelatine) of the capsule wall; thus, the inner wall of the capsule formed by this complex renders the entire wall more resistant to environmental influences.

There are also processes providing the capsule with a suitable outer coat. According to British patent No. 1,159,236, a coat of methacrylic acid or methyl methacrylate is used for this purpose. A coat prepared form silicone resin was also described for the same purpose (Pharm. Ind. 1954, 518–520).

A drawback of the above processes that are aimed at increasing the stability of soft gelatine capsules is that, in addition to the gelatine, the use of another materials is also required.

DESCRIPTION OF THE PRESENT INVENTION

The aim of the present invention is to develop a process for the preparation of soft gelatine capsules for containing bioactive native oils as active ingredients, which provide highly stable soft gelatine capsules being free from additives and useful to protect the therapeutically valuable components of the native oils.

The invention is based on the recognition that the dissociated, negatively charged fatty acid molecules of the saturated and unsaturated free fatty acid content of native oils interact with gelatine which is positively charged hydrophilic polymer to form a complex; thus, the outer wall of the soft gelatine capsule is made of the positively charged hydrophilic polymer (gelatine), whereas the inner wall is a complex formed from the positively charged hydrophilic polymer and the dissociated, negatively charged fatty acid molecules.

The inner wall thus formed renders the capsule extremely resistant to outside environmental influences and on the other hand, it represents a stable barrier that inhibits the dissolution of the active ingredient into the capsule wall.

Thus, according to the process of the invention, the free fatty acid content of the oil used for therapeutical purposes before filling it into the capsule, is adjusted to lie between defined values within a range according to the acid number of the oil. The lower limit of this range is determined by the free fatty acid content which is sufficient to form a double capsule wall, whereas the upper limit depends on the quality requirements of the oil.

The free fatty acid content of the various native oils varies within rather broad limits as governed by a number of factors.

The lower limit of the free fatty acid content is a value characteristic of the given plant species or animal species and mainly depends on the composition of the oils obtained; however, this lower limit may also be affected by the cultivating conditions of the oil source, the geographical location, climate, the amount of the moisture and the like. The acid numbers of several cold-pressed oils form plants grown at various sites in Hungary are summarized in Table 1.

TABLE 1

| | Site of origin | | | | |
|---|---|---|---|---|---|
| | Szekszárd | Szilas | Csákány-doroszló | Nádudvar | Szöce |
| Borago oil (oil of Borago officinalis L.) | 31.5 | 6.0 | — | 3.0 | — |
| Sunflower oil | 3.7 | — | — | 0.2 | — |
| Oenothera oil | 2.7 | 1.1 | 1.5 | — | — |
| Pumpkin seed oil | 1.3 | 5.7 | 0.9 | 1.8 | 0.5 |
| Maize-germ oil | — | 0.3 | — | 4.0 | — |

The differences between the acid numbers may be significant even in the case of precisely defined plant species, depending on the conditions and duration of the storage and pressing of the seeds as well as of the storage of the oil obtained. According to our investigations, the acid number of e.g. pumpkin seed oil obtained from Citrullinia Styrica, i.e. the soft-shell variety of *Cucurbita pepo*, was found to vary within a range of 0.5 to 2.5, depending on the conditions of storage and working-up.

The free fatty acid content of oils is particularly strongly influenced by their tendency to go rancid. The alterations occurring while becoming rancid, mainly the oxidative chain splitting affecting the unsaturated and polyunsaturated fatty acids, significantly increase the acid number and at the same time deteriorate the quality such as the peroxide number of the oils.

According to our investigations, generally a free fatty acid content according to an acid number of at least 0.3 to 0.4 is required for encapsulating vegetable oils. The thus formed, dissociated, negatively charged fatty acid molecules enable the closing of the capsule wall of the positively charged hydrophilic polymer after filing the oil into the capsule. It was observed in the course of our further experiments, that suitably the free fatty acid content of the oils is adjusted to a higher value, ie. to a value corresponding to an acid number of at least 0.5 to 3.0, to build up the double capsule wall described above, whereby the use of the oils is made possible for therapeutical purposes, since the stability of the capsules and the retaining of the active ingredient without any deterioration can be thus accomplished for a long period of time, such as several years.

It was observed in our investigations concerning the encapsulation and stability of oils with a higher acid number, that, above a defined acid number value, the shelf life of the active ingredient deteriorated by orders of magnitude, probably due to the beginning of autooxidation processes. The change of the acid number in time, of encapsulated pumpkin seed oils and oenothera oil, which have different acid numbers, are summarized in Table 2. The peroxide values are also shown in addition to the acid numbers, which are more characteristic of the quality of oils than the acid numbers.

TABLE 2

| | Pumpkin seed oil | | | |
|---|---|---|---|---|
| | Acid number | Peroxide number | Acid number | Peroxide number |
| Before encapsulating | 0.80 | 1.3 | 1.8 | 4.0 |
| After two weeks | 0.75 | 1.3 | 1.9 | 4.5 |
| After 1 month | 0.80 | 1.3 | 2.2 | 6.2 |
| After 6 months | 0.80 | 1.5 | 2.2 | 9.0 |
| After two years | 0.80 | 2.4 | 5.0 | 26.0 |

| | Oenothera oil | | | |
|---|---|---|---|---|
| | Acid number | Peroxide number | Acid number | Peroxide number |
| Before encapsulating | 2.7 | 3.5 | 5.0 | 6.3 |
| After two weeks | 2.7 | 3.5 | 5.5 | 8.2 |
| After 1 month | 2.7 | 3.5 | 5.8 | 13.4 |
| After 6 months | 2.7 | 3.7 | 6.2 | 20.0 |
| After two years | 2.9 | 6.0 | 9.0 | 55.0 |

It is clear from Table 2 that the range of acid numbers values required for the preparation of stable capsules and the highest acid number value vary according to the plant species; thus, the upper limit of the suitable acid numbers was investigated and determined for each plant species. According to our measurements, this value, determined by the composition of the oil obtained from the given plant species, was found to be 1.7 in the case of the pumpkin seed oil. However, a suitable stability was observed in the case of borago oil when an oil with an acid number of 4.0 was encapsulated. Accordingly, the range of suitable acid numbers which in accordance with the present invention is characteristic of a given native oil species is referred to herein as the "effective acid number range." The effective acid number range can be determined for any given native oil by routine experimentation, and these effective acid number ranges are given herein for a large number of therapeutically active native oils. The outside limits of all effective acid number ranges for the therapeutically active native oils are from 0.3 to 4.5".

According to our investigations, the optimum acid number for encapsulation could most simply be adjusted by mixing oils originating from identical plant species and having different free fatty acid content. However, considering that the acid number is increased by the rancidity of the oils, no oils are useful for adjusting the optimum acid number values which have an acid number higher than the maximum value satisfying stability requirements and defined for the given plant species.

The acid number can be optionally adjusted by mixing oils obtained from various plant species. For this purpose, it is preferred to use the oil obtained from the pumpkin seed of Citrullinia Styrica, i.e. a soft-shell variety of *Cucurbita pepo*, because of its advantageous properties such as the low acid number and peroxide number as well as its high tocopherol content.

In the course of another study, it has been stated that the plant parts, such as the seeds, can be collected, stored and treated for obtaining the oil required for therapeutical use, directly after their harvest under conditions promoting retention of the highest amount of valuable components of the active ingredient. Thus, the oils are obtained suitably by pressing, even in those cases when an extraction process is available from the prior art, such as in the case of garlic oil. Thereby, it can be achieved that the oil is obtained without any alteration of its original composition, and the usually unadvantageous selectivity of the solvent processes, which is due to the different solubility of the components, can be avoided. In addition, the storage of the plant parts, such as seeds, is suitably carried out below 15° C., preferably at a temperature between 0° C. and 10° C. Similarly, it is suitable to store the oils obtained at a temperature between 5° C. and 10° C. with the exclusion of air, preferably under nitrogen, until their encapsulation.

Thus, according to the process of the invention, the free fatty acid content of vegetable oils suitably stored below 15° C. and pressed at a temperature between 5° C. and 10° C. is adjusted to an acid number of 0.3 to 4.5 by mixing oils originating from identical or different plant species and having different free fatty acid content, then the oil is filled into soft gelatine capsules in a manner known per se. There are plant oils containing among other components also those that have an unpleasant odor, such as garlic oils. Therefore, the capsule wall can be aromatized by adding a pharmaceutically acceptable scent or perfume, such as coffee, or orange aroma.

The process of the invention is illustrated in detail by the following examples.

EXAMPLE 1

Capsules Filled with Pumpkin Seed Oil

The pumpkin seed oil was obtained by pressing the seeds stored at 0° C. to 5° C. of Citrullinia Styrica L., ie. the soft-shell variety of *Cucurbita pepo* (Cucurbitaceae), at 5° C. to 10° C.

The acid number of the oil was 0.6; the peroxide number was 0.8.

The soft gelatine capsules were prepared in a MARK-type encapsulating equipment.

Each capsule contained 300 mg of oil.

Satisfactory stability of the product was retained for 2 years.

EXAMPLE 2

Capsules Filled with Pumpkin Seed Oil

The pumpkin seed oil was obtained by pressing at 10° C. according to Example 1.

The acid number of the oil was 1.4.

The oil obtained was mixed in a 1:1 ratio with pumpkin seed oil having an acid number of 0.6.

The acid number of the oil mixture was 1.1; the peroxide number was 7.0.

The pumpkin seed oil thus obtained was encapsulated as described in Example 1.

Satisfactory stability of the product was retained for 2 years.

EXAMPLE 3

Capsules Filled with the Oil of *Borago officinalis* L.

Borago oil was obtained by pressing at 10° C. the leaves and stem stored at 10° C. to 15° C. of *Borago officinalis* L. (Boraginaceae). The acid numbers of the oils originating from various places were as follows:

Szilas: 3.8

Szekszárd 4.7

Budakalász: 3.0

Nádudvar: 3.2

The obtained oils with various acid numbers were mixed, except of the oil with the acid number of 4.7.

The acid number of the oil mixture was 3.5; the peroxide number was 9.0.

The mixture thus obtained was encapsulated according to Example 1.

Satisfactory stability of the product was retained for 2 years.

EXAMPLE 4

Capsules Filled with Oenothera Oil or a Mixture of Oenothera and Pumpkin Seed Oil The active ingredient was obtained by pressing at 10° C. the seeds stored at 8° C. to 10° C. of *Oenothera biennis* L. (Onagraceae).

The acid numbers of the oils originating from various Hungarian sites were as follows:

Budakalász: 0.4

Szekszárd: 2.8

Szilas: 0.9

Csákánydoroszló 1.5

The oils with acid numbers of 0.4 and 0.9 were encapsulated according to Example 1. The oils with the acid numbers 2.8 and 1.5 were mixed in a 3:1 ratio with pumpkin seed oil having an acid number of 0.6.

The acid number of the oil mixture was 1.5; the peroxide number was 9.0.

The mixture thus obtained was encapsulated as described in Example 1.

Satisfactory stability of the product was retained for 2 years.

EXAMPLE 5

Capsules Filled with a Mixture of Garlic Oil and Oenothera Oil

Garlic oil was obtained by pressing at 10° C. the bulbs of *Allium sativum* L. (Liliaceae).

The garlic oil was mixed in a 1:8 ratio with oenothera oil and the oil mixture thus obtained was encapsulated as described in Example 1, but by using gelatine scented by adding 3% by mass of coffee aroma.

Each capsule contained 267 mg of oenothera oil and 33 mg of garlic oil.

Satisfactory stability of the product was retained for 2 years.

EXAMPLE 6

Capsules Filled with Cod-Liver Oil

The active ingredient was in this case cod-liver oil of codfish such as *Gadus morrbua* L. and other Gadus species (Gadidae).

The acid number of the oil was 2.0; the peroxide number was 11.0.

The cod-liver oils was encapsulated as described in Example 1 by using gelatine scented by 5% by mass of orange aroma.

The capsules prepared by using the process according to the invention which contain native oils as active ingredient are pharmaceutical compositions free of preservative agents and other additives, the stability of which is provided by the double capsule wall for several years. According to biochemical and clinical investigations carried out, the biological activity was completely retained during the period of stability (i.e. for 2 years).

It was shown by toxicological, pharmacological and clinical studies of the capsules that the active ingredient is atoxic and free of side-effects.

The therapeutical results obtained with encapsulated pumpkin seed oil were highly favorable. The serum lipid levels of hyperlipidemic patients treated under clinical conditions for one month were changed after treatment lasting 36.3 statistically average days as follows: The cholesterol/HDL (HDL means: high density lipoproteins) ratio was increased by 1.72, the triglyceride level by 1.37 mmoles/litre and the cholesterol level by 1.58 mmoles/litre.

It can be stated on the basis of the above results that the compositions are of the few compositions that increase the endogenous HDL cholesterol level which plays a decisive role in the prevention of arteriosclerosis and similarly causes a significant decrease in the triglyceride level which aggravates the disease. The ratio of total cholesterol/HDL is also significantly improved whereby the progression of the arteriosclerosis is also inhibited owing to the increase in the HDL level.

Similarly favorable results were obtained by using borago and oenothera oil.

The encapsulated pumpkin seed oil also proved to have a very preferable effect on patients suffering from prostate hypertrophy. A clinical study was carried out on 60 patients with treatment lasting 8 weeks. In 70% of the patients, the urine retention caused by the benign prostate hypertrophy was eliminated or at least decreased to a great extent. At 95% of the patients, the number of the very frequent urination was normalized. the urinary residue was eliminated or decreased to the minimum at 60% of the patients.

We claim:

1. A process for the preparation of a stable, soft gelatine capsule containing a therapeutically active native oil obtained in the case of vegetable oils by cold pressing oil bearing part of the originating vegetable, said therapeutically active native oil having no preservative for the oil added to it, which consists essentially of determining the acid number of the oil, adjusting the free fatty acid content of the native oil to an acid number within the effective acid number range for that oil, said effective acid number range being between 0.3 and 4.5, said step of adjusting being carried out by mixing the oil with the same or a different native oil having a maximum acid number of 4.5, and filling the oil into a soft gelatine capsule.

2. The process of claim 1, wherein the native oil is a vegetable oil, the pressing of the oil bearing part of the vegetable is carried out at the temperature of from about 0° C. to about 20° C. from oil bearing parts of plants having been stored prior to pressing at a maximum temperature of 15° C.

3. The process of claim 1, wherein the native oil is a vegetable oil, the pressing of the oil bearing part of the vegetable is carried out at the temperature of from about 5° C. to about 10° C. from oil bearing parts of plants having been stored prior to pressing at a maximum temperature of 15° C.

4. The process of claim 1, wherein the oil is stored a maximum temperature of 15° C. in the substantial absence of air, until it is filled into a soft gelatine capsule.

5. The process of claim 1, wherein the oil is stored at a maximum temperature of between about 5° C. to about 10° C. in the substantial absence of air, until it is filled into a soft gelatine capsule.

6. The process of claim 1, wherein the oil is stored a maximum temperature of 15° C. under nitrogen atmosphere, until it is filled into a soft gelatine capsule.

7. The process of claim 1, wherein said adjusting the free fatty acid content of the oil is carried out by adding pumpkin seed oil thereto.

8. The process of claim 1, wherein said adjusting the free fatty acid content of the oil is carried out by adding pumpkin seed oil having an acid number of from 0.5 to 1.0 thereto.

9. The process of claim 1, wherein said native oil is pumpkin seed oil obtained by pressing the seeds of Cucurbitaceae and the acid number of the oil is adjusted to from 0.5 to 1.7.

10. The process of claim 1, wherein said native oil is pumpkin seed oil obtained by pressing the seeds of Cucurbitaceae and the acid number of the oil is adjusted to from 0.5 to about 1.0.

11. The process of claim 1, wherein said native oil is borago oil obtained by pressing the flowery leafed sprouts of Boraginaceae and the acid number of the oil is adjusted to from 0.5 to 4.0.

12. The process of claim 1, wherein said native oil is borago oil obtained by pressing the flowery leafed sprouts of Boraginaceae and the acid number of the oil is adjusted to from 0.5 to 3.5.

13. The process of claim 1, wherein said native oil is oenothera oil obtained by pressing the blooming part of Onagraceae and the acid number of the oil is adjusted to from 0.4 to 3.0.

14. The process of claim 1, wherein said native oil is oenothera oil obtained by pressing the blooming part of Onagraceae and the acid number of the oil is adjusted to from 0.4 to 2.0.

15. The process of claim 1, wherein said native oil is cod-liver obtained from the liver of Gadidae and the acid number of the oil is adjusted to from 1.0 to 4.0.

16. The process of claim 1, wherein said native oil is cod-liver obtained from the liver of Gadidae and the acid number of the oil is adjusted to from 1.0 to 2.5.

* * * * *